United States Patent
Grass et al.

(10) Patent No.: US 7,660,382 B2
(45) Date of Patent: Feb. 9, 2010

(54) EXAMINATION APPARATUS FOR PERFUSION STUDIES

(75) Inventors: Michael Grass, Buchholz in der Nordheide (DE); Volker Rasche, Wellesley (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 119 days.

(21) Appl. No.: 11/570,778

(22) PCT Filed: Jun. 24, 2005

(86) PCT No.: PCT/IB2005/052095

§ 371 (c)(1),
(2), (4) Date: Dec. 18, 2006

(87) PCT Pub. No.: WO2006/003578

PCT Pub. Date: Jan. 12, 2006

(65) Prior Publication Data

US 2008/0037700 A1 Feb. 14, 2008

(30) Foreign Application Priority Data

Jun. 28, 2004 (EP) .................. 04300401

(51) Int. Cl.
*A61B 6/00* (2006.01)
(52) U.S. Cl. .................. 378/8; 378/4; 378/196
(58) Field of Classification Search .................. 378/4, 378/8, 196, 197
See application file for complete search history.

(56) References Cited

U.S. PATENT DOCUMENTS

| | | | | |
|---|---|---|---|---|
| 4,672,651 A | | 6/1987 | Horiba et al. | |
| 5,073,910 A | * | 12/1991 | Eberhard et al. | 378/4 |
| 5,396,418 A | * | 3/1995 | Heuscher | 378/15 |
| 5,566,218 A | * | 10/1996 | Nobuta et al. | 378/20 |
| 6,196,715 B1 | * | 3/2001 | Nambu et al. | 378/197 |
| 6,466,640 B1 | * | 10/2002 | Taguchi | 378/15 |
| 6,504,894 B2 | * | 1/2003 | Pan et al. | 378/8 |
| 6,526,117 B1 | * | 2/2003 | Okerlund et al. | 378/8 |
| 6,816,567 B2 | * | 11/2004 | Drummond et al. | 378/16 |
| 6,865,250 B2 | * | 3/2005 | Londt et al. | 378/8 |
| 2002/0131544 A1 | * | 9/2002 | Aradate et al. | 378/4 |
| 2002/0168053 A1 | * | 11/2002 | Schomberg | 378/197 |
| 2003/0072406 A1 | * | 4/2003 | Yang | 378/4 |
| 2003/0202637 A1 | * | 10/2003 | Yang | 378/210 |
| 2004/0017881 A1 | * | 1/2004 | Cesmeli et al. | 378/4 |

(Continued)

OTHER PUBLICATIONS

Kudo et al., An Extended Completeness Condition for Exact Cone-Beam Reconstruction and Its Application, IEEE, 1995, pp. 1710-1714.*

(Continued)

*Primary Examiner*—Edward J Glick
*Assistant Examiner*—Alexander H Taningco

(57) ABSTRACT

The invention relates to an examination apparatus and a method for perfusion studies in a patient (1). According to the method, a rotational X-ray device (10) is moved on a closed, preferably non-planar trajectory (T) while continuously generating projections of the patient (1) after the injection of a contrast agent with an injection device (20). The projections are used by a data processing system (30) in a sliding window technique to reconstruct three-dimensional images of the body volume. The resulting sequence of 3D images may be displayed on a monitor (31) to reveal the desired information about the perfusion process.

15 Claims, 1 Drawing Sheet

U.S. PATENT DOCUMENTS

2004/0125908 A1* 7/2004 Cesmeli et al. ............... 378/4
2006/0285632 A1* 12/2006 Boese et al. ................. 378/8
2008/0031417 A1* 2/2008 Kramp ....................... 378/95

OTHER PUBLICATIONS

Pack et al., Invenstigation of saddle trajectories for cardiac CT imaging in cone-beam geometry, Phys. Med. Biol., 49, 2004, pp. 2317-2336.*

Townsend et al: "Fully Three-Dimensional Reconstruction for a Pet Camera With Retractable Septa"; Nuclear Science Symposium, 1990. Conference Record: Including Sessions on Nuclear Power Systems and Medical Imaging Conference, 1990 IEEE Arlington, VA, USA Oct. 22-27, 1990. IEEE, Oct. 22, 1990, pp. 1222-1227, XP010041451.

Schomberg, H.: "Complete Source Trajectories for C-Arm Systems and a Method for Coping With Truncated Cone-Beam Projections"; 3D-2001-The Sixth International Meeting on Fully Three Dimensional Image Reconstruction in Radiology and Nuclear Medicine, pp. 221-224.

Defrise et al: "A Cone-Beam Reconstruction Algorithm Using Shift-Invariant Filtering and Cone-Beam Projection"; IEEE Trans. Med. Imag., vol. 13, No. 1, pp. 186-195, Mar. 1994.

d'Arcy et al: "Applications of Sliding Window Reconstruction With Cartesian Sampling for Dynamic Contrast Enhanced MRI"; NMR in Biomedicine, vol. 15, No. 2, pp. 174-183, Apr. 2002.

* cited by examiner

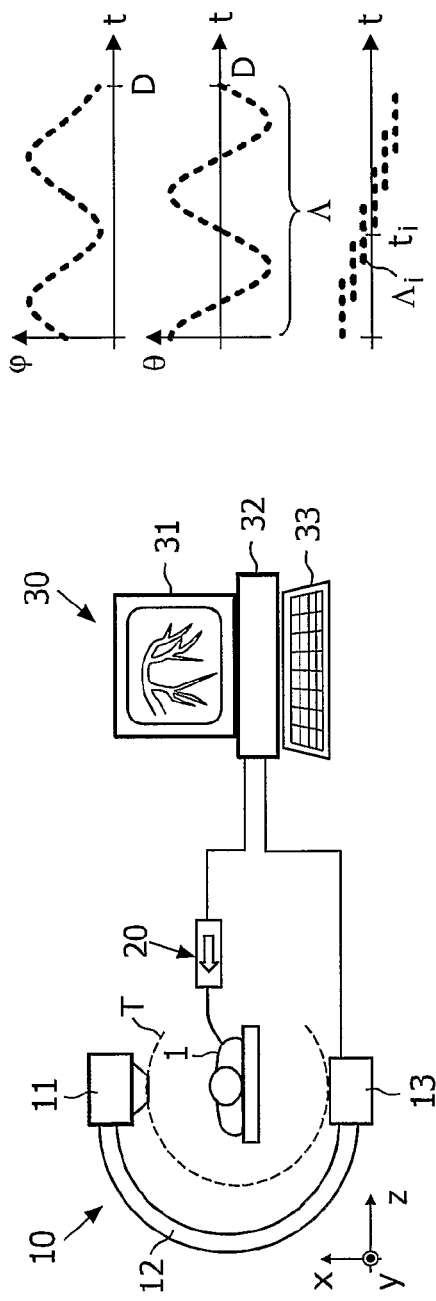
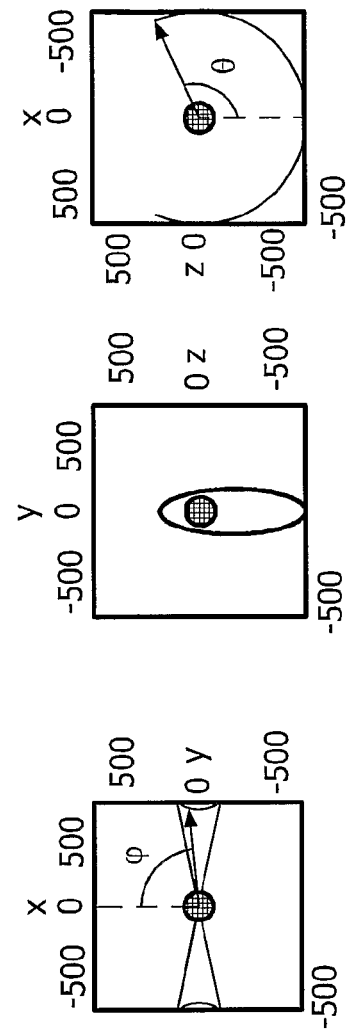
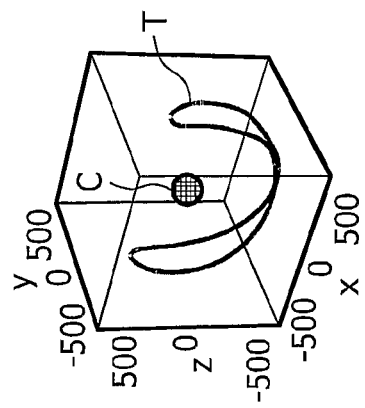

EXAMINATION APPARATUS FOR PERFUSION STUDIES

FIELD OF THE INVENTION

The invention relates to an examination apparatus and a method for the study of dynamic processes in a body volume, particularly of perfusion, as well as a record carrier with software for the execution of said method.

BACKGROUND OF THE INVENTION

The study of perfusion processes in the body volume of a patient is necessary for the diagnosis of cardiovascular diseases. Such perfusion studies typically involve the injection of a bolus of a contrast agent via a catheter or intravenously and the generation of a sequence of X-ray projections that show the spreading of said bolus in the vessel system and the surrounding tissue. In complex vessel trees like the cerebral vessel tree, it may however be difficult to judge the observed process based on two-dimensional projections acquired in the angio-suite. This is especially true for brain perfusion, where three-dimensional tomographic images of excellent contrast resolution are required for a careful diagnosis.

SUMMARY OF THE INVENTION

Therefore, it was an object of the present invention to provide means for a more versatile study of dynamic processes, particularly of perfusion in a complex vessel system and the surrounding tissue.

This object is achieved by an examination apparatus according to claim 1, by a method according to claim 9, and by a record carrier according to claim 10. Preferred embodiments are disclosed in the dependent claims.

The examination apparatus according to the present invention may be used for the study of dynamic processes in a body volume. A very important (but not limiting) example that will be in the focus of the following description is the study of perfusion in the vessel system of a patient. The examination apparatus comprises an X-ray device with an X-ray source and an X-ray detector that can be moved relative to an object and a data processing system (computer) that is coupled to the X-ray device in order to control it and to evaluate the generated image data. The examination apparatus is adapted to execute the following steps:

a) The generation of a series of X-ray projections of the body volume along a trajectory during a given duration, said generation being achieved by the X-ray device under the control of the data processing system. A "projection series along a trajectory" means that the projection directions with which a certain point of a body volume is mapped intersect both said point and the trajectory. Such projections may be achieved if the X-ray source moves along said trajectory while emitting X-rays towards the body volume.

b) The reconstruction of a temporal sequence of three-dimensional (3D) images of the body volume, wherein the reconstruction of each 3D image is based on a subset of projections from said series of X-ray projections that were generated during a connected temporal window within the aforementioned duration. Furthermore, the temporal windows are chosen such that they overlap, or, more precisely, that for each temporal window there is at least one other temporal window which partially overlaps with it. The temporal windows may for example have the same size and may be shifted with respect to each other by a small percentage of that size.

The examination apparatus allows the study of dynamic processes like perfusion in complex spatial environments, for example the brain of a patient, because the process is visualized in three-dimensional images. The reconstruction of such 3D images is possible due to the application of trajectories for the X-ray device which allow a continuous movement of the device and the acquisition of enough different projections for three-dimensional (exact) reconstruction methods. Moreover, the evaluation of the series of projections in overlapping temporal windows provides the high temporal resolution which is needed for the observation of the underlying processes and which makes optimal use of the available data. The evaluation of a series of images of a dynamic process in overlapping temporal windows is known as "sliding window approach" from the literature (d'Arcy J A; Collins D J; Rowland I J; Padhani A R; Leach M O: "Applications of sliding window reconstruction with Cartesian sampling for dynamic contrast enhanced MRI", NMR in Biomedicine, vol. 15, no. 2, pp. 174-183, April 2002).

The examination apparatus may further comprise an injection device for the controlled injection of a contrast agent into the vessel system of patient. The injection device may be adapted to be manually controlled by the medical staff. Alternatively, said injection device may be coupled to and controlled by the data processing system. The use of controlled injections makes the examination apparatus suited for perfusion studies in a patient.

The X-ray device preferably comprises an X-ray source and a detector that are rigidly coupled to each other, for example via a C-arm, and that can be moved commonly on the surface of a sphere or a part of such a surface. In this case projections of a body volume located at the centre of said sphere can be produced from different directions, thus providing the necessary data for exact three-dimensional reconstruction methods.

According to another preferred embodiment of the invention, the trajectory is closed. In this case the X-ray device can repeatedly move along the trajectory while generating projections from identical or similar directions at different times.

The trajectory may be planar, for example an arc along which the X-ray device sweeps continuously back and forth. The trajectory may also be non-planar and preferably of a form that allows the application of exact reconstruction algorithms. A non-planar trajectory may particularly be produced by the superposition of oscillations in azimuthal and polar directions.

Each subset of projections that belong to a certain temporal window and that are used for the reconstruction of a 3D image is preferably just so large that the application of an exact reconstruction method is possible. Then 3D images with high contrast and accuracy can be achieved, while the restriction to a minimal subset of this kind guarantees are good correlation of the 3D image with the situation in the time point that corresponds to the temporal window.

While exact reconstruction methods for the generation of the 3D images are preferred due to their higher accuracy, approximation methods may of course be used, too. Moreover, the reconstruction of the 3D images may be achieved by direct inversion methods or by iterative reconstruction methods which are known to a person skilled in the art.

The projections within a subset or temporal window that are used for the reconstruction of a certain 3D image originate from different time points and therefore represent the observed body volume in different states of the dynamic process. If the temporal window is small compared with the time scale of the dynamic process, the changes of the process during the temporal window may be neglected and the 3D image that is reconstructed from the temporal window may be associated with a certain reference time point, for example the midpoint of the temporal window. According to a further development of the invention, the projections of a subset are applied in the reconstruction method with a weighting factor that corresponds to their temporal distance to said reference time point. Projections that are temporally close to the reference time point are then given a higher weight in the reconstruction than projections far away from said reference time point, because the latter may show the dynamic process in a state that has changed significantly with respect to the reference time point.

The reconstruction method for the 3D images may make use of redundancy compensation functions. In this case the difference of such a redundancy compensation function for two trajectory sections that belong to consecutive subsets is preferably used to update the corresponding 3D images.

The invention further comprises a method for the study of dynamic processes in a body volume, which comprises the following steps:

a) Generating during a given duration a series of X-ray projections of the body volume along a (planar or preferably non-planar) trajectory.

b) Reconstructing a temporal sequence of 3D images of the body volume, wherein each 3D image is based on a subset of projections from said series, the subset belonging to a temporal window within said duration, and wherein said temporal windows overlap.

The method comprises in general form the steps that can be executed with an examination apparatus of the kind described above. Therefore, reference is made to the preceding description for more information on the details, advantages and improvements of that method.

Furthermore, the invention comprises a record carrier, for example a floppy disk, a hard disk, or a compact disc (CD), on which a computer program for the study of dynamic processes in a body volume is stored, said program being adapted to execute the aforementioned method.

These and other aspects of the invention will be apparent from and elucidated with reference to the embodiment(s) described hereinafter.

BRIEF DESCRIPTION OF THE DRAWINGS

In the following the invention is described by way of example with the help of the accompanying drawings in which:

FIG. 1 is a diagrammatic representation of an examination apparatus according to the present invention;

FIG. 2 shows an exemplary closed, non-planar trajectory in a perspective view and in three orthogonal projections;

FIG. 3 illustrates the temporal overlapping of subsets of projections that are used for the 3D reconstruction.

DESCRIPTION OF PREFERRED EMBODIMENTS

FIG. 1 is a principle sketch of an examination apparatus according to the present invention that may be used for perfusion studies in a patient 1. The apparatus comprises a rotational X-ray device 10 which is in the shown example a conventional system with an X-ray source 11 and an X-ray detector 13 that are rigidly connected via a C-arm 12. The X-ray device can be rotated around a point in space such that the X-ray source 11 and the detector 13 move on the surface of a sphere (or at least part thereof) and always face each other diametrically. Thus projections of a body volume in the centre of the sphere, for example of the brain or the heart of a patient 1, can be generated from different directions.

FIG. 2 shows in a perspective and in projections a typical closed, non-planar trajectory T that can be followed by the X-ray source 11 and the detector 13, respectively, during a typical movement of the X-ray device 10. The whole trajectory T lies in the surface of a sphere (not shown) with the centre C. Each point of the trajectory T may the described in spherical coordinates (with the centre C as origin) by a polar angle $\phi$ and an azimuthal angle $\theta$. The temporal course of said angles during the movement of the X-ray device 10 on the trajectory T is principally shown in the upper two diagrams of FIG. 3. If the amplitude of the oscillation in $\theta$ is zero, a planar trajectory results that corresponds to an arc of a circle (extending over 180° plus the fan angle of the beam) and along which the X-ray device 10 repeatedly sweeps back and forth.

Other examples of suited closed, non-planar trajectories may be found in the article "Complete Source Trajectories for C-Arm Systems and a Method for Coping with Truncated Cone-Beam Projections" (H. Schomberg in: 3D-2001—The Sixth International Meeting on Fully Three-Dimensional Image Reconstruction in Radiology and Nuclear Medicine, pp. 221-224), which is incorporated into the present application by reference.

FIG. 1 further shows a data processing system 30 that comprises a computer 32 to which a monitor 31 and an input device like a keyboard 33 are connected. The computer 32 is further connected to the X-ray device 10 in order to control the exposures and to evaluate the generated projections. The computer 32 comprises typical components like central processing unit, memory, I/O interfaces and the like together with appropriate software in order to fulfill the functions that are described in more detail below. The computer 32 may particularly reconstruct 3D images of the target area of the patient 1 from projections from different directions generated by the X-ray device 10. These 3D images may then be displayed on a monitor 31 for a user.

Moreover, FIG. 1 depicts an injection device 20 by which for example a contrast agent can be injected into the vessel system of the patient 1 in a controlled way. Typically, the injection system comprises a motor driven syringe with contrast agent, and a catheter that runs from the syringe into the body of the patient, ending at the region of interest in the vessel system. The injection device 20 may be manually controlled or be coupled to the computer 32 such that it can be controlled by the computer and/or that it can transmit data about its function to the computer.

In order to study a dynamic process like perfusion in the vessel system of the patient 1, the described examination apparatus will be used in a way which leads to 3D volume information of adequate temporal resolution by utilizing exact reconstruction methods for planar or non-planar source orbits combined with sliding window reconstruction principles. It is suggested to use a closed, non-planar acquisition trajectory T like that in FIG. 2 for perfusion imaging. Cone beam projection data are acquired for the time interval [0, D], in which the perfusion process takes place, by covering the closed trajectory T for multiple times using a continuous system movement. The sampling of the projection acquisition may be constant or variable in time. The acquisition takes place at the maximum system speed to guarantee high temporal resolution.

The full series of generated projections covering the trajectory T for multiple times is marked by $\Lambda$ in FIG. 3 (wherein each dot represents one projection). It may be subdivided into overlapping subsets $\Lambda_i$ each of which corresponds to a certain temporal window and which are preferably large enough to enable exact reconstruction of the volume of interest. These subsets/temporal windows are chosen with equal or variable spacing in the temporal domain.

To each subset $\Lambda_i$ of the series $\Lambda$ an exact reconstruction method is applied, for example the method described by Defrise and Clack (M. Defrise, R. Clack: "A cone-beam reconstruction algorithm using shift-invariant filtering and cone-beam back projection", IEEE Trans. Med. Imag., vol. 13, no. 1, pp. 186-195, March 1994), taking the redundancy of the 3D Radon data into account in a correct manner. If for example the trajectory of the X-ray source is parameterized by a parameter $\lambda$, each source position for projection acquisition can be described by a vector $\zeta(\lambda)$. A Radon plane measured from such a source position is then characterized by its normal vector $\xi$, i.e. all vectors x lying in that plane fulfill $(x-\zeta(\lambda))\cdot\xi=0$. With $\rho=\zeta(\lambda)\cdot\xi$, a Radon value is generated at R $f(\rho\xi, \lambda)$, wherein R f is the Radon transform of a function f. One Radon value can be generated by more than one source position $\lambda$. Since exact reconstruction requires complete sampling of the Radon space and correct handling of the redundancies, a redundancy compensation function is introduced into the back projection formula according to $$M_i(\xi, \lambda) = \frac{1}{n_i(\xi, \lambda)}, \quad (1)$$

where $n_i(\xi, \lambda)$ means that a specific Radon value can be delivered several times by a set of projections $\Lambda_i$. For practical reasons allowing discrete implementation a differentiable and normalized version of $M_i(\xi, \lambda)$ is used in the back projection expression.

From the complete series $\Lambda$ of available projections (multiple covered trajectory) the subset $\Lambda_i$ (centered at a reference time point $t_i$) which enables exact reconstruction of the volume of interest can now be selected by an appropriate redundancy compensation function $M_i(\xi, \lambda)$. For optimal computational performance, the difference of the redundancy compensation function of two trajectory intervals may be used to update the reconstructed volume originating from the trajectory part $\Lambda_{i+1}$ with respect to the volume result from $\Lambda_i$. Using this acquisition approach, the exact reconstruction of the same volume at multiple time steps $t_i$ with a temporal resolution $\Delta t_i$ is feasible.

Any other suitable exact or approximate reconstruction method may also be used, which is capable to process projection data acquired along non-planar orbits and to deliver excellent contrast resolution. Apart from direct inversion schemes, also iterative reconstruction methods may be applied.

Temporal resolution can be improved using varying temporal gating functions that weight projections near the reference time point ti higher than those that are further away. The result of this sliding window 3D reconstruction can be used as input for 3D perfusion analysis of a target structure.

Finally it is pointed out that in the present application the term "comprising" does not exclude other elements or steps, that "a" or "an" does not exclude a plurality, and that a single processor or other unit may fulfill the functions of several means. Moreover, reference signs in the claims shall not be construed as limiting their scope.

The invention claimed is:

1. Examination apparatus for the study of dynamic processes in a body volume, comprising an X-ray device and a data processing system which are adapted to execute the following steps:

generating during a given duration a series of X-ray projections of the body volume along a closed trajectory, wherein the trajectory is non-planar and produced by independent oscillations in azimuthal and polar directions;

reconstructing a sequence of 3D images of the body volume, wherein each 3D image is based on a subset of projections from said series, wherein the subsets belong to temporal windows within said duration, and wherein said temporal windows overlap.

2. The examination apparatus according to claim 1, further comprising an injection device for injection of contrast agent.

3. The examination apparatus according to claim 1, wherein the X-ray device comprises an X-ray source and a detector that are rigidly coupled to each other and that can be moved on a sphere or a part thereof.

4. The examination apparatus according to claim 1, wherein the subsets of projections comprise just enough projections for an exact reconstruction method.

5. The examination apparatus according to claim 1, wherein the projections of a subset are used in the reconstruction method with a weight that corresponds to their temporal distance to a reference time point.

6. The examination apparatus according to claim 1, wherein a difference of a redundancy compensation function for two trajectory sections that belong to consecutive subsets is used to update the corresponding 3D images.

7. A method for the study of dynamic processes in a body volume, comprising the following steps:

generating during a given duration a series of X-ray projections of the body volume along a non-planar trajectory that is produced by independent oscillations in azimuthal and polar directions;

reconstructing a sequence of 3D images of the body volume, wherein each 3D image is based on a subset of projections from said series, wherein the subsets belong to temporal windows within said duration, and wherein said temporal windows overlap, and wherein the projections of the subset are used in the reconstruction with a weight that corresponds to their temporal distance to a reference time point.

8. The method of claim 7, further comprising injecting contrast agent into the body volume.

9. The method of claim 7, wherein the trajectory is closed.

10. The method of claim 7, wherein a difference of a redundancy compensation function for two trajectory sections that belong to consecutive subsets is used to update the corresponding 3D images.

11. The method of claim 7, wherein the trajectory is a single, repeating trajectory.

12. A storage medium on which a computer program for the study of dynamic processes in a body volume is stored, said program being adapted to cause a computer to:

generate during a given duration a series of X-ray projections of the body volume along a closed trajectory;

reconstruct a sequence of 3D images of the body volume, wherein each 3D image is based on a subset of projections from said series, wherein the subsets belong to temporal windows within said duration, and wherein said temporal windows overlap, and wherein the projections of the subset are used in the reconstruction with a weight that corresponds to their temporal distance to a reference time point.

13. The storage medium of claim 12, wherein the program is adapted to use a non-planar trajectory that is produced by independent oscillations in azimuthal and polar directions.

14. The storage medium of claim 12, wherein the program is adapted to utilize a difference of a redundancy compensation function for two trajectory sections that belong to consecutive subsets to update the corresponding 3D images.

15. The storage medium of claim 12, wherein the trajectory is a single, repeating trajectory.

* * * * *